United States Patent
Chibret

[11] 4,220,645
[45] Sep. 2, 1980

[54] CHROMONE DERIVATIVES

[75] Inventor: Henri Chibret, Clermont-Ferrand, France

[73] Assignee: Thea (Therapeutique et Applications) SA, France

[21] Appl. No.: 865,573

[22] Filed: Dec. 29, 1977

[30] Foreign Application Priority Data

Jan. 3, 1977 [FR] France ................ 77 00010

[51] Int. Cl.² ............... C07D 413/12; C07D 311/22; A61K 31/35; A61K 31/535
[52] U.S. Cl. .................... 424/248.58; 424/250; 424/267; 424/274; 424/283; 544/151; 544/376; 546/196; 260/345.2; 260/326.5 D
[58] Field of Search ............... 544/151, 376; 260/345.2, 293.58, 326.5 D; 546/196; 424/248.58, 250, 267, 274, 283

[56] References Cited

U.S. PATENT DOCUMENTS 2,897,211 7/1959 Dare .................... 546/196

Primary Examiner—Henry R. Jiles
Assistant Examiner—R. W. Ramsuer
Attorney, Agent, or Firm—Finnegan, Henderson, Farabow, Garrett & Dunner

[57] ABSTRACT

A chromone derivative has the formula:

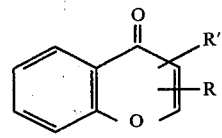

in which one of the radicals R, R' is a hydrogen atom or a lower alkyl radical and the other of the radicals is an aminoalkyl oxy benzoyl group having the formula:

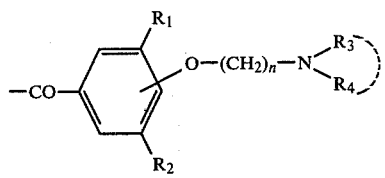

The derivative can be of use in the pharmaceutical industry in drugs for treating heart disorders.

The derivative can be prepared from the novel intermediate compounds:

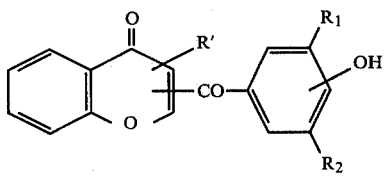

and

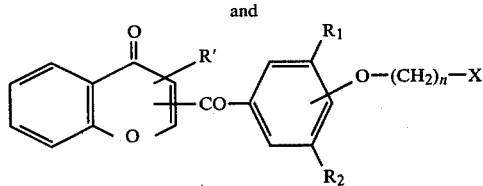

16 Claims, No Drawings

CHROMONE DERIVATIVES

The present invention relates to chromone derivatives having an amino alkyl oxy benzoyl chain, and use thereof in drugs which may be of particular use in the treatment of heart disorders. The invention also relates to a method of preparing these derivatives, and to intermediate compounds used in the preparation thereof.

According to a first aspect of the present invention there is provided a chromone derivative having the general formula:

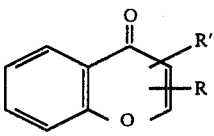

in which one of the radicals R and R' is in the 2 position on the chromone ring and the other of the radicals R and R' is in the 3 position, R' is a hydrogen atom or a lower alkyl radical, and R is the group:

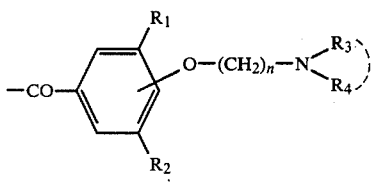

in which both $R_1$ and $R_2$ are a hydrogen atom or a lower alkyl radical, n is an integer of from 1 to 5, $R_3$ and $R_3$ are identical or different and comprise a hydrogen atom or a lower cycloalkyl or alkyl radical, or a hydroxy substituted lower cycloalkyl or alkyl radical or form with the nitrogen atom a heterocyclic ring.

The amino alkyl oxy chain may be in the ortho or para position relative to the carbonyl group.

With reference to the formulae used herein, the term "lower alkyl" generally denotes a straight-chain or branched alkyl radical containing from 1 to 6 carbon atoms. The nitrogen heterocyclic ring may inter alia be of the piperidine, pyrrolidine, morpholine or N-hydroxy ethyl piperazine type.

In preferred derivatives in accordance with the present invention, R' is a hydrogen atom or, when in the 3 position, a lower alkyl radical such as a methyl radical. Preferably the radical R is in the 2 position on the chromone ring.

The preferred values for the radical R are as follows:
$R_1$ is the same as $R_2$ and is a hydrogen atom or a methyl radical;
n is 2,3 4 or 5;
$R_3$ and $R_4$ are an ethyl, n-butyl or 2-hydroxy propyl group; or
$R_3$ is a hydrogen atom and $R_4$ is an isopropyl or terbutyl group; or
$R_3$ is a cyclohexyl group and $R_4$ is a methyl or isopropyl group; or
$R_3$ and $R_4$ combine with the nitrogen atom to form a heterocyclic ring such as piperidine, pyrrolidine, morpholine or N-hydroxy ethyl piperazine.

Advantageously, $R_1$ and $R_2$ are methyl groups when R is in the 2 position on the chromone ring.

Derivatives in accordance with the present invention can be in free form or in the form of their salts of addition with pharmaceutically acceptable acids, for example the hydrochloride or iodomethylates.

Preferred derivatives include:
2-[4-(3N,N-dibutylamino propoxy) 3,5-dimethyl benzoyl] chromone hydrochloride,
3-[4-(3-N,N-dibutylamino propoxy) 3,5-dimethyl benzoyl] chromone hydrochloride,
2-[2-(3-N,N-dibutylamino propoxy) benzoyl] chromone hydrochloride,
2-[4-(2-N,N-diethylamino ethoxy) benzoyl] chromone hydrochloride,
2-[4-(3-N,N-dibutylamino propoxy) benzoyl] chromone hydrochloride,
2-[4-(3-N,N-dibutylamino propoxy) 3,5-dimethyl benzoyl] 3-methyl chromone hydrochloride,
2-[4-(2-N,N-dibutylamino ethoxy) 3,5-dimethyl benzoyl] chromone hydrochloride,
2-[4-(3-N-isopropylamino propoxy) 3,5-dimethyl benzoyl] chromone hydrochloride,
2-[4-(3-N,-terbutylamino propoxy) 3,5-dimethyl benzoyl] chromone hydrochloride,
2-[4-(N,-cyclohexyl 3-N-isopropylamino propoxy) 3,5-dimethyl benzoyl] chromone hydrochloride,
2-[4-(3-morpholino propoxy) 3,5-dimethyl benzoyl] chromone iodomthylate,
2-[4-(N-hydroxyethyl 3-piperazino) 3,5-dimethyl benzoyl] chromone hydrochloride,
3-[4-(3-N,N-diisopropanolamino propoxy) 3,5-dimethyl benzoyl] chromone hydrochloride,
2-[4-(3-N-piperidino propoxy) 3,5-dimethyl benzoyl] chromone iodomethylate,
2-[4-(N-methyl 3-N-cyclohexoamino propoxy) 3,5-dimethyl benzoyl] chromone iodomethylate,
2-[4-(4-N,N-dibutylamino butoxy) 3,5-dimethyl benzoyl] chromone iodomethylate,
2-[4-(5-N,N-dibutylamino pentoxy) 3,5-dimethyl benzoyl] chromone iodomethylate, and
2-[4-(3-N-pyrrolidino propoxy) 3,5-dimethyl benzoyl] chromone iodomethylate.

Derivatives in accordance with the present invention can be of pharmacological use since they normally have remarkable anti-arrythmic, bradycardiac, antitachycardiac and sympathico-inhibiting properties.

According to a second aspect of the present invention there is provided a pharmaceutical composition comprising a derivative of the first aspect and a pharmaceutically acceptable carrier or diluent.

According to a third aspect of the present invention there is provided a method of treating heart disorders, which comprises administering a non-toxic dosage of a pharmaceutical composition in accordance with the second aspect.

The derivatives are, advantageously, the active principle of the compositions. These pharmaceutical compositions, when proportioned to the medicinal weight, can be used as drugs for use in the therapy of various disorders. More particularly, they can be used for treating angina and various disturbances of the heart rhythm. The daily dosages in human therapy are, advantageously, of the order of from 200 to 1200 mg. They may be administered together with additives and excipients in the various galenic forms, for example in tablets or pills containing from 50 to 300 mg, advantageously, containing 100 or 200 mg.

According to a fourth aspect of the present invention there is provided a method of preparing a chromone derivative using a compound having the general formula (II):

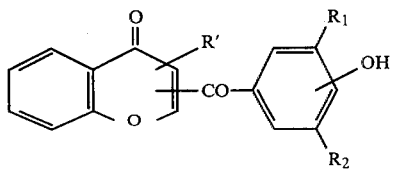

in which both $R_1$ and $R_2$ are a hydrogen atom or a lower alkyl radical and in which R' is a hydrogen atom or a lower alkyl radical.

According to a fifth aspect of the present invention there is provided a method of preparing a chromone derivative using a compound having the general formula (III):

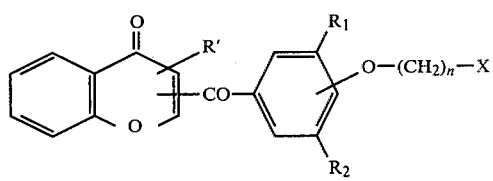

in which both $R_1$ and $R_2$ are a hydrogen atom or a lower alkyl radical, in which R' is a hydrogen atom or a lower alkyl radical, in which x is a halogen atom and in which n is an integer of from 1 to 5.

According to a sixth aspect of the present invention there is provided a method of preparing a chromone derivative, which method comprises reacting a phenol and 2-carboxylic or 3-carboxylic chromone acid chloride as follows:

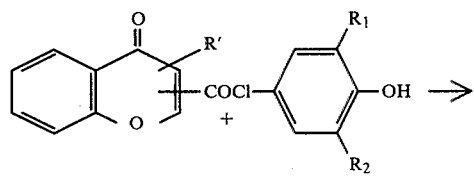

in which R' is a hydrogen atom or a lower alkyl radical and in which both $R_1$ and $R_2$ are a hydrogen atom or a lower alkyl radical and reacting the compound having the general formula (II), with an amine having the general formula (IV) as follows:

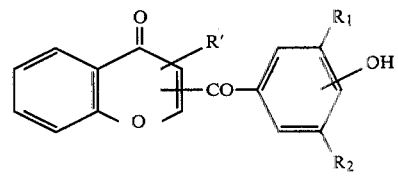

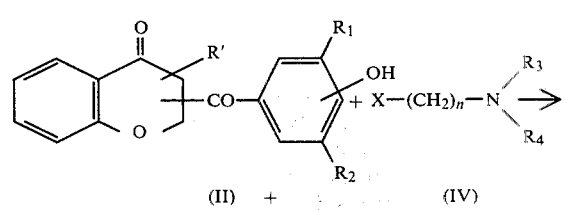

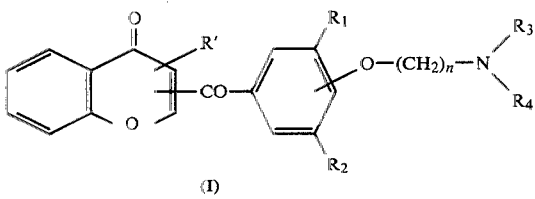

in which $R_3$ and $R_4$ are identical or different and comprise a hydrogen atom or a lower cycloalkyl or alkyl radical or a hydroxy substituted lower cycloalkyl or alkyl radical or form with the nitrogen atom a heterocyclic ring, in which X is a halogen atom and in which n is an integer of from 1 to 5.

According to a seventh aspect of the present invention there is provided a method of preparing a chromone derivative, which method comprises reacting a phenol and a 2-carboxylic or 3-carboxylic chromone acid chloride as follows:

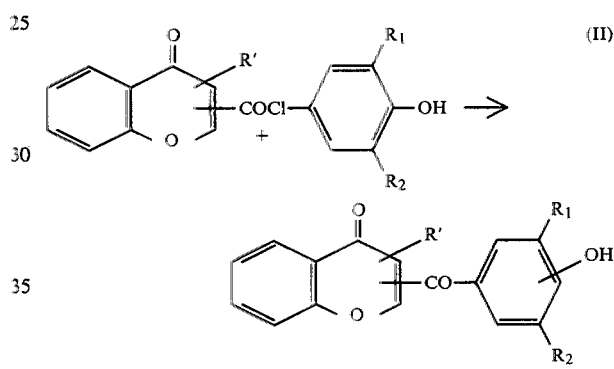

in which R' is a hydrogen atom or a lower alkyl radical and in which both $R_1$ and $R_2$ are a hydrogen atom or a lower alkyl radical, reacting, in a first step, the compound having the general formula (II) with a dihalogenoalkane having the general formula (V) as follows:

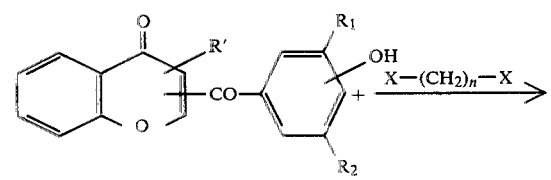

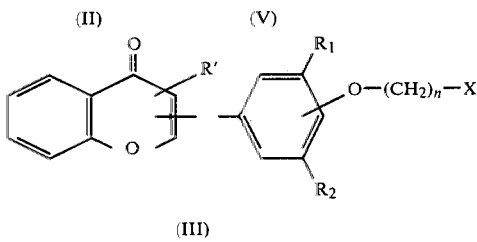

in which X is a halogen atom and in which n is an integer of from 1 to 5 and reacting, in a second step, the compound having the general formula (III) with a primary or secondary amine as follows:

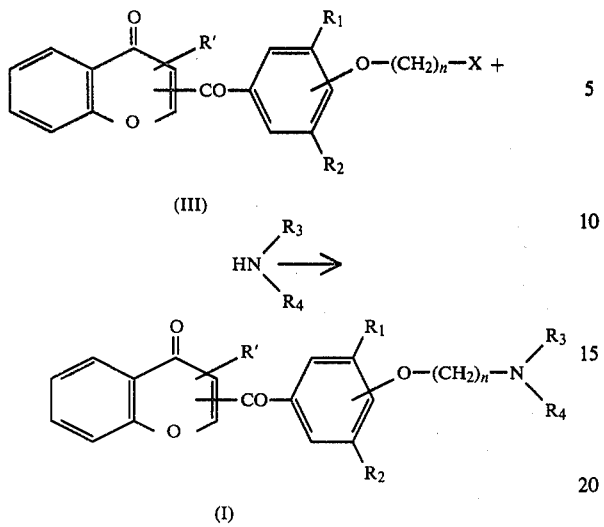

(III)

(I)

in which $R_3$ and $R_4$ are identical or different and comprise a hydrogen atom or a lower cycloalkyl or alkyl radical, or an hydroxy substituted lower cycloalkyl or alkyl radical or can form with the nitrogen atom a heterocyclic ring.

A derivative in accordance with the present invention can advantageously be obtained in a series of steps, the first of which is a Friedel-Craft reaction between 2-carboxylic or 3-carboxylic chromone acid chloride and a phenol, substituted if required, as shown below:

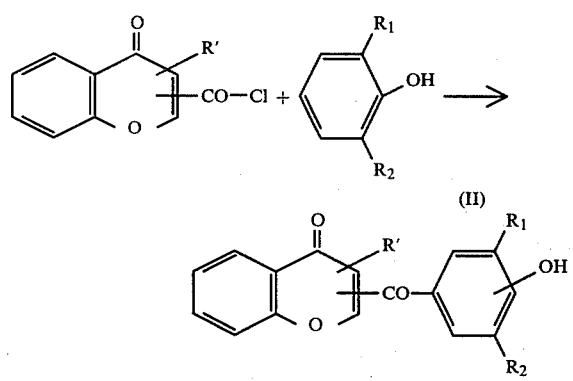

(II)

In this reaction, R', $R_1$ and $R_2$ are as previously designated.

The preparation of 3-carboxylic chromone acid chloride is described in Japanese Pat. No. 4,725,181. 2-carboxylic chromone acid chloride is a product known in the literature. Its preparation is described in French Pat. B S M No. 5574 M. These products may also contain a lower alkyl substituent in the 2 or 3 position, respectively. The formula (II) compound, a phenol derivative, is novel and constitutes an intermediate product in the preparation of formula (I) derivatives.

In the second step, the formula II compound is reacted either with a compound having the general formula:

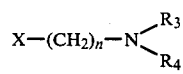

X being a halogen atom, advantageously, chlorine or bromine, and $R_3$ and $R_4$ being as previously designated. The reaction diagram is as follows.

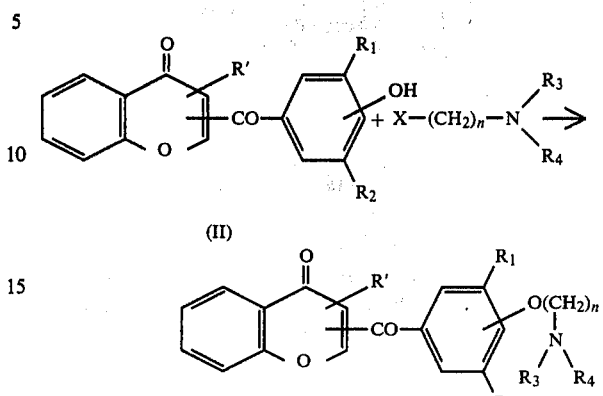

(II)

or the formula (II) compound is reacted with a dihalogenoalkane having the formula $X—(CH_2)_n—X$, where X is a halogen atom, inter alia chlorine or bromine, thus obtaining a formula (III) intermediate product as follows:

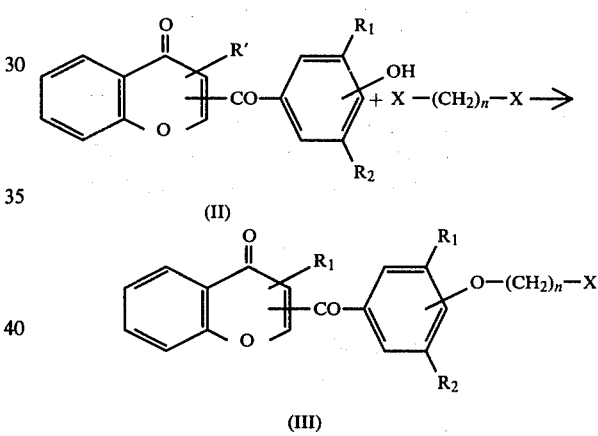

(III)

The formula III intermediate product can then react with a primary or secondary amine to give a formula (I) derivative. The reaction scheme is as follows:

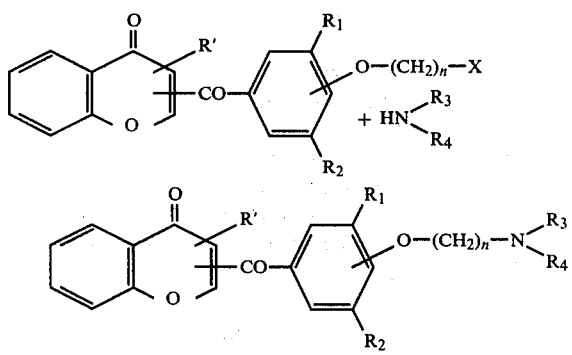

According to an eighth aspect of the present invention there is provided a compound, such as an intermediate compound in the preparation of a chromone derivative, having the general formula:

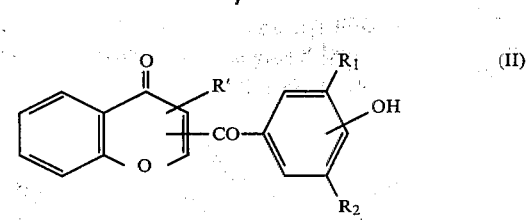

in which R' is a hydrogen atom or a lower alkyl radical and in which both $R_1$ and $R_2$ are a hydrogen atom or a lower alkyl radical.

According to a ninth aspect of the present invention there is provided a compound, such as an intermediate in the preparation of a chromone derivative, having the general formula:

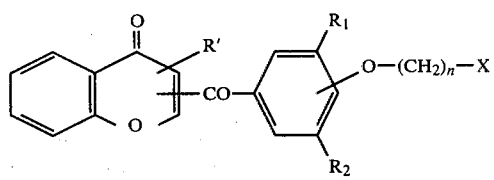

in which R' is a hydrogen atom or a lower alkyl radical, in which both $R_1$ and $R_2$ are a hydrogen atom or a lower alkyl radical, in which n is an integer of from 1 to 5 and in which X is a halogen atom.

According to a tenth aspect of the present invention there is provided a method of preparing a compound, which method comprises reacting a phenol and a 2-carboxylic or 3-carboxylic chromone acid chloride as follows:

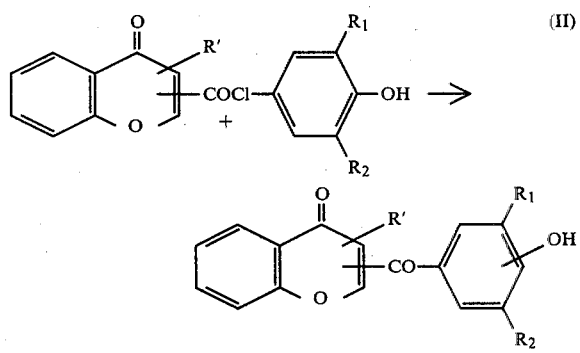

in which R' is a hydrogen atom or a lower alkyl radical and in which both $R_1$ and $R_2$ are a hydrogen atom or a lower alkyl radical.

According to an eleventh aspect of the present invention there is provided a method of preparing a compound, which method comprises reacting a phenol and a 2-carboxylic or 3-carboxylic chromone acid chloride as follows:

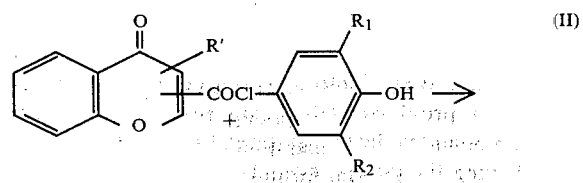

in which R' is a hydrogen atom or a lower alkyl radical and in which both $R_1$ and $R_2$ are a hydrogen atom or a lower alkyl radical, and reacting the compound having the general formula (II) with a dihalogenoalkane having a general formula (V) as follows:

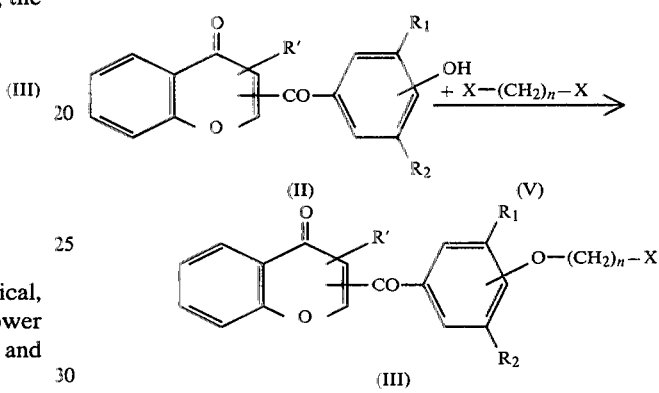

in which n is an integer from 1 to 5 and X is a halogen atom.

The following Examples further illustrate the present invention.

PREPARATION OF HYDROXY BENZOYL CHROMONES

EXAMPLE I 3,5-dimethyl 4-hydroxy 2-benzoyl chromone was prepared from 2-carboxylic chromone acid chloride and 2,6-dimethyl phenol, as follows:

1,2 mol of an electrophilic catalyst, advantageously aluminium chloride, was slowly added to a solution of 48.8 g (0.4 mol) of 2,6-dimethyl phenol in 400 ml of dichloroethane and agitated at ambient temperature for an hour. The mixture was cooled to 0° C. and a solution of 84 g (0.4 mol) of 2-carboxylic chromone acid chloride in 400 ml of a neutral solvent, such as dichloroethane, was slowly added. Agitation was continued at 0° C. for 5 hours and then at ambient temperature for 4 days.

The reaction mixture was poured into 1.6 liters of iced 50% hydrochloric acid. The resulting precipitate was filtered, washed with water, dried and recrystallised from dioxane. The product was 106 g 2-(3,5-dimethyl 4-hydroxy benzoyl) chromone—a 72% yield. Melting-point: 216° C.

EXAMPLE II

The following were prepared in the same manner:

(1) 2-4(-hydroxy benzoyl) chromone and (2) 2-(2-hydroxy benzoyl) chromone were prepared from 2-carboxylic chromone acid chloride and phenol. The para hydroxyl derivative was soluble in dichloroethane and was recrystallised from absolute ethanol. The yield was 54%. The ortho hydroxy derivative, soluble in dichloroethane, was recrystallised from ethanol. The yield was 11%.

(3) 2-(3,5-dimethyl 4-hydroxy benzoyl) 3-methyl chromone was prepared from 2-carboxylic chromone 3-methyl acid chloride and 2,6-dimethyl phenol.

(4) 3-(3,5-dimethyl 4-hydroxy benzoyl) chromone was prepared from 3-carboxylic chromone acid chloride and 2,6-dimethyl phenol. In this case, the reaction occurred with reflux for 6 hours. The yield was 59%.

The elementary analysis and melting-points of these intermediate products are given in Table I hereinafter.

EXAMPLE III (1) 2-[4-(3-N,N-dibutylamino propoxy) 3,5-dimethyl benzoyl] chromone hydrochloride (compound No. 1) was prepared as follows from the appropriate hydroxy benzoyl chromone and amine:

6.9 g (0.05 mol) of potassium carbonate was added to a solution of 29.4 g (0.1 mol) of 2-(3,5-dimethyl 4-hydroxy benzoyl) chromone in 250 ml of dimethyl formamide and kept at 100° C. for an hour. A solution of 20.5 g (0.1 mol) of 3 N,N-dibutylamino 1-chloropropane in 100 ml of diethyl formamide was then added and the resulting solution heated to 130° C. for 3 hours. The mineral salts were filtered, the dimethyl formamide was concentrated, dissolved in 300 ml water and extracted twice with 200 ml of benzene. The organic phase was dried on magnesium sulphate and the hydrochloride was precipitated by adding hydrochloric ether. The precipitate was recrystallised from an acetone/ether mixture. The product was 40 g of 2-[4-(3-N,N-dibutylamino propoxy) 3,5-dimethyl benzoyl] chromone. The yield was 80%.

The following products were prepared in the same manner, starting from the corresponding hydroxybenzoyl chromones and amines:

(2) 3-[4-(3-N,N-dibutylamino propoxy) 3,5-dimethyl benzoyl] chromone hydrochloride (compound No. 2);

(3) 2-[2-(3-N,N-dibutylamino propoxy) benzoyl] chromone hydrochloride (compound No. 3);

(4) 2-[4-(2-N,N-diethylamino ethoxy) benzoyl] chromone hydrochloride (compound No. 4);

(5) 2-[4-(3-N,N-dibutylamino propoxy) benzoyl] chromone hydrochloride (compound No. 5);

(6) 2-[4-(3-N,N-dibutylamino propoxy) 3,5-dimethyl benzoyl] 3-methyl chromone hydrochloride (compound No. 6);

(7) 2-[4-(2-N,N-dibutylamino ethoxy) 3,5-dimethyl benzoyl] chromone hydrochloride (compound No. 7).

The elementary analysis of the aforementioned products in shown in Table II hereinafter.

EXAMPLE IV

2-[4-(3-N-isopropylamino propoxy) 3,5-dimethyl benzoyl] chromone hydrochloride (compound No. 8) was prepared as follows via the corresponding formula (III) derivative:

2-[4-(3-bromo propoxy) 3,5-dimethyl benzoyl] chromone.

(1) The formula (III) derivative was prepared as follows:

27.6 g (0.2 mol) of potassium carbonate was added to a solution of 29.4 g (0.1 mol) of 2-(3,5-dimethyl 4-hydroxy benzoyl) chromone in 150 ml of dimethyl formamide, 101 g (0.5 mol) of 1,3-dibromo propane was added and the admixture left at ambient temperature for 15 hours with constant agitation. The potassium bromide precipitate was filtered, the dimethyl formamide was concentrated in vacuo and the residue dissolved in 300 ml of water. Extraction was effected with 200 ml of methylene chloride, and precipitation was then effected by adding 200 ml of ether. The product was 36 g of 2-[4-(3-bromo propoxy) 3,5-dimethyl benzoyl] chromone.

The yield was 86%. Melting-point: 104° C.

The following formula (III) derivatives were obtained in the same manner:

(2) 2-[4-(4-bromo butoxy) 3,5-dimethyl benzoyl] chromone, M.P.=76° C.

(3) 2-[4-(5-bromo pentoxy) 3,5-dimethyl benzoyl] chromone, M.P.=70° C.

2-[4-(3-N-isopropylamino propoxy) 3,5-dimethyl benzoyl] chromone hydrochloride (compound No. 8) was obtained as follows:

14 g (0.034 mol) of 2-[4-(3-bromo propoxy) 3,5-dimethyl benzoyl] chromone was dissolved in 150 ml of dimethyl formamide and 2.4 g (0.017 mol) of potassium carbonate and 2.2 g (0.038 mol) of isopropylamine were added. The resulting admixture was heated for one hour in an oil bath at 100° C., the resulting mineral salts were eliminated by filtration, and the filtrate was concentrated to dryness. After extraction with ether and drying of the organic phase, a stream of hydrochloric acid was bubbled through. The precipitating hydrochloride was collected by filtration. The product was 12 g of 2-[4-(3-N-isopropylamino propoxy) 3,5-dimethyl benzoyl] chromone hydrochloride.

The yield was 83%. Melting-point: 235° C.

The same method and the corresponding amines were used to obtain the following products:

2-[4-(3-N,-terbutylamino propoxy) 3,5-dimethyl benzoyl] chromone (compound No. 9);

2-[4-(N,-cyclohexyl 3-N-isopropylamino propoxy) 3,5-dimethyl benzoyl] chromone hydrochloride (compound No. 10);

2-[4-(3-N-morpholino propoxy) 3,5-dimethyl benzoyl] chromone iodomethylate (compound No. 11);

2-[4-(N-hydroxyethyl 3-piperazino) 3,5-dimethyl benzoyl] chromone hydrochloride (compound No. 12);

2-[4-(3-N,N-diisopropanolamino propoxy) 3,5-dimethyl benzoyl] chromone hydrochloride (compound No. 13);

2-[4-(3-N-piperidino propoxy) 3,5-dimethyl benzoyl] chromone iodomethylate (compound No. 14);

2-[4-(N-methyl 3-N-cyclohexoamino propoxy) 3,5-dimethyl benzoyl] chromone iodomethylate (compound No. 15);

2-[4-(4-N,N-dibutylamino butoxy) 3,5-dimethyl benzoyl] chromone iodomethylate (compound No. 16);

2-[4-(5-N,N-dibutylamino pentoxy) 3,5-dimethyl benzoyl] chromone iodomethylate (compound No. 17);

2-[4-(3-N-pyrrolidino propoxy) 3,5-dimethyl benzoyl] chromone iodomethylate (compound No. 18).

The melting-points and elementary analysis of the aforementioned products are given in Table III hereinafter.

EXAMPLE V

Anti-arrhythmic activity in the guinea-pig

Reference: Experimental evaluation of anti-arrhythmic drugs in the guinea-pig. GUIDICELLI, WITCHITZ, LARNO, BOISSIER, Biomedecine, 1973, 19, 308–313.

Male and female guinea-pigs were used, weighing from 600 to 800 g and anesthetised with urethane (1.25 g/kg/I.P.), tracheotomised and kept under artificial respiration. The electrocardiogram (D₂) was recorded.

Arrhythmia was produced by perfusion at the rate of 0.5 ml/min of an aqueous solution of aconitine nitrate (0.15 mg/ml) in the jugular vein. Measurements were made of the time before the following rhythm disturbances appeared:

Polymorphic extrasystoles (PES),
Ventricular tachycardia (VT),
Multifocal ventricular tachycardia (MVT),
Ventricular tachycardia bursts (VTB), that is a sequence of ventricular complexes of fixed frequency but with regular increasing and decreasing amplitude.

The following substances were used:
Compound No. 1,
Compound No. 7, and
Amiodarone hydrochloride for comparison.

The substances were intravenously injected immediately before perfusion with aconitine had started.

The results are shown in Table IV hereinafter.

Compounds 1 and 7 were found to delay rhythm disorders induced by aconitine to a greater extent than the conventional reference compound, amiodarone. Consequently, since aconitine increases the excitability of the myocardium, compounds 1 and 7 may be of use in treating rhythmic disorders due to myocardiac hyperexcitability.

EXAMPLE VI

Bradycardiac activity on the conscious dog

The dogs used were male and female mongrels weighing from 15 to 20 kg. Their bypass electrocardiograms (D₂) were recorded and their heart rate (F$_C$) was measured with a cardiotachometer.

The animals were not used to tests and consequently their heart rate was relatively high, 130 beats per minute on average.

3 control measurements of the heart rate were made during the hour before intravenous injection of the substance under study, and 3 further measurements were made 5 minutes, 20 minutes and 35 minutes after administration.

Compound No. 1, when administered to a conscious dog in the dose of 4 mg/kg/I.V. significantly lowers the spontaneous heart rate. This bradycardiac activity of compound No. 1 can be used in treating angina, since a reduction in the heart rate helps to relieve the load on the heart, which is one of the aims in treating this disease.

EXAMPLE VII

Sympathico-inhibiting activity in the conscious dog

The dogs used were male and female mongrels weighing from 15 to 20 kg. The animals were not anaesthetised. Their electrocardiograms (D₂) and heart rates were measured.

Short bouts of tachycardia, approx. 1 minute long, were produced by intravenously injecting a solution of isoprenaline in doses of 0.25 Y/kg. The injections were repeated every 15 minutes until the increase in heart rate had been reproduced in a satisfactory manner.

Next, the substance under study was intravenously injected and 3 additional measurements of the isoprenaline tachycardia were made 5 minutes, 20 minutes and 35 minutes after the product under study had been administered.

The results are shown in Table VI hereinafter.

Thus, compound No. 1 has a sympathico-inhibiting activity since it can moderate tachycardia produced by isoprenaline stimulation of the sympathico$\beta$ receptors of the heart in a conscious dog.

This property can be used in the treatment of angina, since it is known what an important part it plays by the orthosympathetic system in the mechanism of haemodynamic disturbances accompanying an angina crisis.

EXAMPLE VIII

Acute toxicity in the mouse

The acute toxicity of compound No. 6 administered intravenously (I.V.) and orally (P.O.) was determined in female mice of the Swiss strain weighing from 25 to 27 g.

Compound No. 6 was administered in aqueous solution in a concentration of 0.4% intravenously and in a concentration of 1% and 4% orally.

The lethal doses were of the order of 30 mg/kg I.V. and 1200 mg/kg P.O.

EXAMPLE IX

Tablets for use in human medicine may advantageously have the following composition:

2-[4-(3-N,N-dibutylamino propoxy) 3,5-dimethyl benzoyl] chromone hydrochloride (compound No. 1) 200 mg. Excipient: q.s. for 1 tablet.

The daily dose is from 1 to 6 tablets.

EXAMPLE X

Pills for use in human medicine may advantageously have the following composition:

2-[4-(2-N,N-dibutylamino ethoxy) 3,5-dimethyl benzoyl] chromone hydrochloride (compound No. 7): 100 mg. Excipient q.s. for 1 pill.

The daily dose is from 3 to 10 pills.

Of course, the invention is not limited to the Examples given hereinbefore but can be varied in numerous ways known to the skilled addressee, depending on the desired applications.

TABLE I

[Structure: chromone with R' at position 2 and R at position 3]

| R or R' position 2 | R or R' position 3 | M.P. °C. | Elementary Analysis | C % | H % |
|---|---|---|---|---|---|
| —CO—C₆H₄—OH (para) | H | 201 | Calc. | 72,17 | 3,78 |
| | | | Found | 71,88 | 3,97 |
| —CO—C₆H₄—OH (ortho, HO) | H | 120 | Calc. | 72,17 | 3,78 |
| | | | Found | 71,11 | 4,22 |
| —CO—C₆H₂(CH₃)₂—OH | H | 120 | Calc. | 73,46 | 4,79 |
| | | | Found | 73,20 | 5,05 |
| —CO—C₆H₂(CH₃)₂—OH | CH₃ | 223 | Calc. | 74,01 | 5,23 |
| | | | Found | 73,72 | 5,16 |
| H | —CO—C₆H₂(CH₃)₂—OH | 230 | Calc. | 73,46 | 4,79 |
| | | | Found | 72,53 | 5,30 |

TABLE II

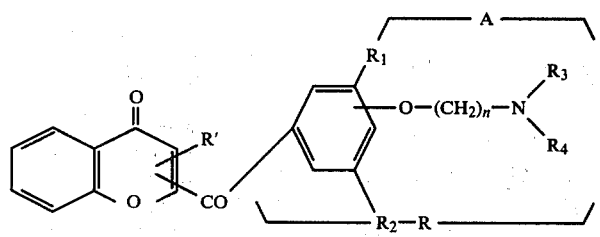

| Compound No. | Position R | R' | Position A | n | $R_1 = R_2$ | $R_3 = R_4$ | M.P. °C. | | C % | H % | N % | Cl % |
|---|---|---|---|---|---|---|---|---|---|---|---|---|
| 1 | 2 | H | -p | 3 | —CH₃ | n C₄H₉ | 100 | calc. | 69,65 | 7,66 | 2,80 | 7,09 |
| | | | | | | | | found | 69,17 | 7,60 | 2,83 | 7,15 |
| 2 | 3 | H | -p | 3 | —CH₃ | n C₄H₉ | 114 | calc. | 69,65 | 7,66 | 2,80 | 7,09 |
| | | | | | | | | found | 69,15 | 7,57 | 2,99 | |
| 3 | 2 | H | -o | 3 | H | n C₄H₉ | 130 | calc. | 68,70 | 7,26 | 2,97 | 7,51 |
| | | | | | | | | found | 67,95 | 7,06 | 3,17 | 7,33 |
| 4 | 2 | H | -p | 2 | H | C₂H₅ | 179 | calc. | 65,75 | 6,02 | 3,49 | |
| | | | | | | | | found | 65,39 | 6,04 | 3,47 | |
| 5 | 2 | H | -p | 3 | H | n C₄H₉ | 90 | calc. | 68,70 | 7,26 | 2,97 | 7,51 |
| | | | | | | | | found | 67,48 | 7,01 | 3,26 | 7,50 |
| 6 | 2 | 3-CH₃ | -p | 3 | CH₃ | n C₄H₉ | 148 | calc. | 70,09 | 7,84 | 2,72 | 6,90 |
| | | | | | | | | found | 69,48 | 7,66 | 2,66 | 6,86 |
| 7 | 2 | H | -p | 2 | CH₃ | n C₄H₉ | 160 | calc. | 69,19 | 7,47 | 2,88 | 7,29 |
| | | | | | | | | found | 69,22 | 7,38 | 2,92 | 7,35 |

TABLE III

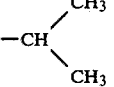

| Compound | n | R₃ | R₄ | B | M.P. °C. | | Elementary Analysis C % | H % | N % |
|---|---|---|---|---|---|---|---|---|---|
| 8 | 3 | H | -CH(CH₃)₂ | HCl | 235 decomp. | Calc. Found | 67,05 66,73 | 6,56 6,48 | 3,26 3,29 |
| 9 | 3 | H | -C(CH₃)₃ | HCl | 230 | Calc. Found | 67,63 67,53 | 6,81 6,84 | 3,16 2,96 |
| 10 | 3 | -CH(CH₃)CH₃ | cyclohexyl | HCl | 150 | Calc. Found | 70,36 69,58 | 7,48 7,54 | 2,74 3,35 |
| 11 | 3 | tetrahydropyranyl | | ICH₃ | 236 | Calc. Found | 55,42 55,39 | 5,37 5,56 | 2,49 2,44 |
| 12 | 3 | piperidyl-N-CH₂-CH₂OH | | HCl | 200 decomp. | Calc. Found | 60,34 60,02 | 6,38 7,07 | 5,21 4,95 |
| 13 | 3 | -CH₂-CHOH-CH₃ | -CH₂-CHOH-CH₃ | HCl | 170 | Calc. Found | 64,34 64,26 | 6,80 6,80 | 2,98 2,78 |
| 14 | 3 | cyclohexyl ring | | ICH₃ | 250 | Calc. Found | 57,76 57,29 | 5,74 5,30 | 2,49 2,42 |
| 15 | 3 | -CH₃ | cyclohexyl | ICH₃ | 246 | Calc. Found | 59,09 58,57 | 6,16 6,03 | 2,38 2,55 |
| 16 | 4 | -(CH₂)₃CH₃ | -(CH₂)₃-CH₃ | ICH₃ | 140 | Calc. Found | 60,09 60,03 | 6,83 6,79 | 2,26 2,06 |
| 17 | 5 | -(CH₂)₃-CH₃ | -(CH₂)₃-CH₃ | ICH₃ | 120 | Calc. Found | 60,66 60,76 | 7,00 7,07 | 2,21 2,27 |
| 18 | 3 | cyclopentyl ring | | ICH₃ | 200 | Calc. Found | 57,04 56,71 | 5,52 5,66 | 2,56 2,50 |

TABLE IV

| Substance | Dose mg/kg/I.V. | No. of guinea pigs | Average time for arrhythmia to appear (in secs) | | | |
|---|---|---|---|---|---|---|
| | | | PES | VT | MTV | VTB |
| Controls | — | 17 | 27 ± 2 | 30 ± 2 | 41 ± 2 | 63 ± 4 |
| Compound No. 1 | 2 | 6 | 63 ± 4 | 79 ± 9 | 94 ± 10 | 139 ± 11 |
| Compound No. 7 | 4 | 6 | 36 ± 4 | 55 ± 8 | 77 ± 9 | 145 ± 10 |
| Amiodarone (hydrochloride) | 4 | 6 | 32 ± 3 | 44 ± 6 | 59 ± 5 | 94 ± 8 |

TABLE V

| Substance Dose | No. of dogs | Average heart rate before substance injected (beats/min) | Average heart beat after substance injected | | |
|---|---|---|---|---|---|
| | | | 5 min | 20 min | 35 min |
| Compound No. 1 4mg/kg/I.V. | 9 | 132 ± 9 | 114 ±10 (S) | 109 ±8 (S) | 107 ±8 (S) |

(S) = significant to p = 0,05

TABLE VI

| Substance Dose | No. of dogs | Effect of isoprenaline before substance injected Average heart beat (beats per minute) | Effect of isoprenaline after substance injected. | | |
|---|---|---|---|---|---|
| | | | 5 min | 20 min | 35 min |
| Compound No. 1 4 mg/kg/I.V. | 6 | 114 ± 9 (controls) | 68 ±12 (S) | 89 ±10 (S) | 97 ±10 (S) |

(S) = significant to P = 0,05

What is claimed is:

1. A chromone derivative having the general formula:

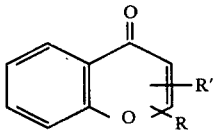

in which one of the radicals R and R' is in the 2 position on the chromone ring and the other of the radicals R and R' is in the 3 position, R' is a hydrogen atom or a lower alkyl radical, and R is the group:

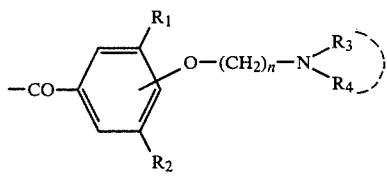

in which
both $R_1$ and $R_2$ are a hydrogen atom or a lower alkyl radical,
n is an integer of from 1 to 5,
$R_3$ and $R_4$ are identical or different and comprise a hydrogen atom or a lower cycloalkyl radical or a hydroxy substituted lower cycloalkyl or alkyl radical, or form with the nitrogen atom a heterocyclic ring selected from the group consisting of pyrrolidine, piperidine, morpholine and N-hydroxy ethyl piperazine.

2. The derivative of claim 1, wherein R' is a hydrogen atom when in the 2 position.

3. The derivative of claim 1, wherein R' is a lower alkyl radical when in the 3 position.

4. The derivative of claim 3, wherein R' is a methyl radical.

5. The derivative of claim 1, wherein $R_1$ is the same as $R_2$ and is a hydrogen atom or a methyl group and wherein n is 2, 3, 4 or 5.

6. The derivative of claim 1, wherein $R_3$ and $R_4$ are an ethyl, n-butyl or 2-hydroxy propyl group.

7. The derivative of claim 1, wherein $R_3$ is a hydrogen atom and $R_4$ is an isopropyl or terbutyl group.

8. The derivative of claim 1, wherein $R_3$ is a cyclohexyl group and $R_4$ is a methyl or isopropyl group.

9. The derivative of claim 1, wherein $R_3$ and $R_4$ combine with the nitrogen atom to form a heterocyclic ring selected from the group consisting of pyrrolidine, piperidine, morpholine and N-hydroxy ethyl piperazine.

10. The derivative of claim 1, which is in the form of a salt of addition of a pharmaceutically acceptable acid.

11. The derivative of claim 1, wherein R is in the 2 position on the chromone ring.

12. The derivative of claim 1, which is selected from the group consisting of
2-[4-(3N,N-dibutylamino propoxy)3,5-dimethyl benzoyl] chromone hydrochloride,
3-[4-(3-N,N-dibutylamino propoxy)3,5-dimethyl benzoyl] chromone hydrochloride,
2-[2-(3-N,N-dibutylamino propoxy) benzoyl] chromone hydrochloride,
2-[4-(2-N,N-diethylamino ethoxy) benzoyl] chromone hydrochloride,
2[4-(3-N,N-dibutylamino propoxy) benzoyl] chromone hydrochloride,
2-[4-(3-N,N-dibutylamino propoxy) 3,5-dimethyl benzoyl] 3-methyl chromone hydrochloride,
2-[4-(2-N,N-dibutylamino ethoxy) 3,5-dimethyl benzoyl] chromone hydrochloride,
2-[4-(3-N-isopropylamino propoxy) 3,5-dimethyl benzoyl] chromone hydrochloride,
2-[4-(3-N, terbutylamino propoxy) 3,5-dimethyl benzoyl] chromone hydrochloride
2[4-(N, cylcohexyl 3-N-isopropylamino propoxy) 3,5-dimethyl benzoyl]chromone hydrochloride,
2-[4-(3-N-morpholino propoxy) 3,5-dimethyl benzoyl] chromone iodomethylate,
2-[4-(N-hydroxyethyl 3-piperazino) 3,5-dimethyl benzoyl] chromone hydrochloride
2-[4-(3-N,N-diiasopropanolamino propoxy) 3,5-dimethyl benzoyl] chromone hydrochloride,
2-[4-(3-N-piperidino propoxy) 3,5-dimethyl benzoyl] chromone iodomethylate, 2-[4-(N-methyl 3-N-cyclohexoamino propoxy) 3,5-dimethyl benzoyl] chromone iodomethylate,
2-[4-(4-N,N-dibutylamino butoxy) 3,5-dimethyl benzoyl] chromone iodomethylate,
2-[4-(5-N, N-dibutylamino pentoxy) 3,5-dimethyl benzoyl] chromone iodomethylate, and
2-[4-(3-N-pyrrolidino propoxy) 3,5-dimethyl benzoyl] chromone iodomethylate.

13. A pharmaceutical composition useful in treating arrhythmia, bradycardia, tachycardia, and heart disorders necessitating sympathico inhibition comprising an effective amount of a derivative of claim 1 and a pharmaceutically acceptable carrier or diluent.

14. The pharmaceutical composition of claim 13, which is in a tablet or pill form containing from 50 to 300 mg.

15. The pharmaceutical composition of claim 14 which is in tablet or pill form containing 100 or 200 mg.

16. A method of treating arrhythmia, bradycardia, tachycardia, and heart disorders necessitating sympathico inhibition which comprises administering an effective amount of a non-toxic dosage of the pharmaceutical composition of claim 13.

* * * * *